United States Patent
Cipriano (10) Patent No.: US 9,198,816 B2
(45) Date of Patent: Dec. 1, 2015

(54) AUXILIARY CONTROLS FOR INFANT CARE APPARATUS

(71) Applicant: General Electric Company, Schenectady, NY (US)

(72) Inventor: James Patrick Cipriano, Ellicott City, MD (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 119 days.

(21) Appl. No.: 13/721,745

(22) Filed: Dec. 20, 2012

(65) Prior Publication Data

US 2014/0179984 A1    Jun. 26, 2014

(51) Int. Cl.
*A61G 11/00*    (2006.01)
*A61B 5/01*    (2006.01)
*A61B 5/00*    (2006.01)

(52) U.S. Cl.
CPC ............... *A61G 11/009* (2013.01); *A61B 5/01* (2013.01); *A61G 11/00* (2013.01); *A61B 5/7435* (2013.01); *A61B 2503/045* (2013.01); *A61B 2505/03* (2013.01); *A61B 2560/0242* (2013.01); *A61G 2203/16* (2013.01); *A61G 2203/20* (2013.01)

(58) Field of Classification Search
CPC . A61G 11/009; A61G 11/00; A61G 2203/20; A61G 2203/16; A61B 5/7435; A61B 5/01; A61B 2503/045; A61B 2505/03; A61B 2560/0242; G01G 19/44
USPC ............. 119/304, 315, 311; 236/2, 91, 91 R; 200/61; 600/22, 301; 237/3, 14; 435/303.1, 809; 128/920; D24/163
See application file for complete search history.

(56) References Cited

U.S. PATENT DOCUMENTS

| | | |
|---|---|---|
| 4,936,824 A | 6/1990 | Koch et al. |
| 5,376,761 A | 12/1994 | Koch et al. |
| 5,474,517 A | 12/1995 | Falk et al. |
| 5,817,003 A * | 10/1998 | Moll et al. ............... 600/22 |
| 6,213,935 B1 | 4/2001 | Mackin et al. |
| 6,409,665 B1 | 6/2002 | Scott et al. |
| 6,956,175 B1 | 10/2005 | Daly et al. |
| 7,038,588 B2 | 5/2006 | Boone et al. |
| 7,255,671 B2 | 8/2007 | Boone et al. |
| 7,282,022 B2 | 10/2007 | Falk et al. |
| 7,311,657 B2 | 12/2007 | Boone et al. |
| 7,357,811 B2 | 4/2008 | Dykes et al. |
| 7,364,539 B2 | 4/2008 | Mackin et al. |
| 7,442,163 B2 | 10/2008 | Ten Eyck et al. |
| 7,927,269 B2 | 4/2011 | Ten Eyck et al. |
| 2001/0049465 A1 | 12/2001 | Goldberg et al. |

(Continued)

OTHER PUBLICATIONS

International Search Report and Written Opinion—Application PCT/US13/75983, mail date Feb. 24, 2014, 9 pages.

*Primary Examiner* — Christine H Matthews
*Assistant Examiner* — Sunita Reddy (57) ABSTRACT

An infant care station includes a horizontal surface configured to support an infant patient wherein at least one wall extends generally vertically from the horizontal surface. The horizontal surface and at least one wall define a microenvironment. A processor operates a display mounted to the care station at a location external to the microenvironment to present a graphical user interface. An auxiliary input device is located within the microenvironment, is communicatively connected to the processor, and is configured for operation by a clinician to interact with the graphical user interface.

18 Claims, 6 Drawing Sheets

(56) References Cited

U.S. PATENT DOCUMENTS

| | | |
|---|---|---|
| 2002/0044059 A1 | 4/2002 | Reeder et al. |
| 2002/0082468 A1 | 6/2002 | Goldberg et al. |
| 2002/0103432 A1 | 8/2002 | Kawchuk |
| 2002/0173696 A1* | 11/2002 | Kolarovic et al. .............. 600/22 |
| 2002/0196141 A1 | 12/2002 | Boone et al. |
| 2003/0153805 A1 | 8/2003 | Gryn et al. |
| 2004/0236174 A1 | 11/2004 | Boone et al. |
| 2004/0236175 A1 | 11/2004 | Boone et al. |
| 2005/0124866 A1 | 6/2005 | Elaz et al. |
| 2005/0133027 A1 | 6/2005 | Elaz et al. |
| 2005/0143632 A1 | 6/2005 | Elaz et al. |
| 2005/0215844 A1* | 9/2005 | Ten Eyck et al. ............... 600/22 |
| 2007/0149843 A1 | 6/2007 | Ten Eyck et al. |
| 2008/0183029 A1 | 7/2008 | Mackin et al. |
| 2009/0009468 A1* | 1/2009 | Zhu et al. ...................... 345/158 |
| 2009/0043204 A1 | 2/2009 | Pelissier et al. |
| 2009/0149927 A1 | 6/2009 | Kneuer et al. |
| 2009/0256817 A1 | 10/2009 | Perlin et al. |
| 2012/0116150 A1* | 5/2012 | Falk et al. ...................... 600/22 |

* cited by examiner

AUXILIARY CONTROLS FOR INFANT CARE APPARATUS

BACKGROUND

The present disclosure relates to an infant care apparatus. More specifically, the present disclosure relates to auxiliary controls for the infant care apparatus.

An infant care apparatus is used in the care of infants, particularly neonates in order to provide a controlled environment within which the infant is contained to promote the wellbeing of the infant. The infant care apparatus defines a microenvironment that surrounds the infant patient. The infant care apparatus operates to control environmental conditions of the microenvironment, such as oxygen, temperature, humidity, and light in such a manner as to promote the health and wellbeing of the infant patient.

An infant care apparatus may also provide a physical or other environmental barrier such that the microenvironment is sterile or partially sterile in order to reduce the risks of infection to the infant patient.

BRIEF DISCLOSURE

A non-limiting exemplary embodiment of an infant care station includes a horizontal surface configured to support an infant patient where at least one wall extends generally vertically from the horizontal surface. The horizontal surface and at least one wall define a microenvironment configured to extend about the infant patient. A touch-sensitive display is mounted to the care station at a location external to the microenvironment. A processor operates the touch-sensitive display to present a graphical user interface. The auxiliary input device is located within the microenvironment and is communicatively connected to the processor. The auxiliary input device is configured for operation by clinician to interact with the graphical user interface presented by the touch-sensitive display.

A further non-limiting exemplary embodiment of an infant care station maintains environmental conditions about an infant patient. A horizontal surface is configured to support the infant patient. At least one wall extends generally vertically from the horizontal surface. A canopy is positioned above the horizontal surface and extends generally parallel to the horizontal surface. A microenvironment is defined by the horizontal surface, the canopy and at least one wall. A touch-sensitive display is mounted to the infant care station at a location external to the microenvironment. A processor is communicatively connected to the touch-sensitive display and configured to operate a touch-sensitive display to present a touch-sensitive graphical user interface. An auxiliary input device is positioned within the microenvironment and is communicatively connected to the processor. Upon activation of the auxiliary input device, the processor presents a cursor in the touch-sensitive graphical user interface and the auxiliary input device controls the cursor within the touch-sensitive graphical user interface to interact with the graphical user interface.

DETAILED DISCLOSURE

Figure 1:
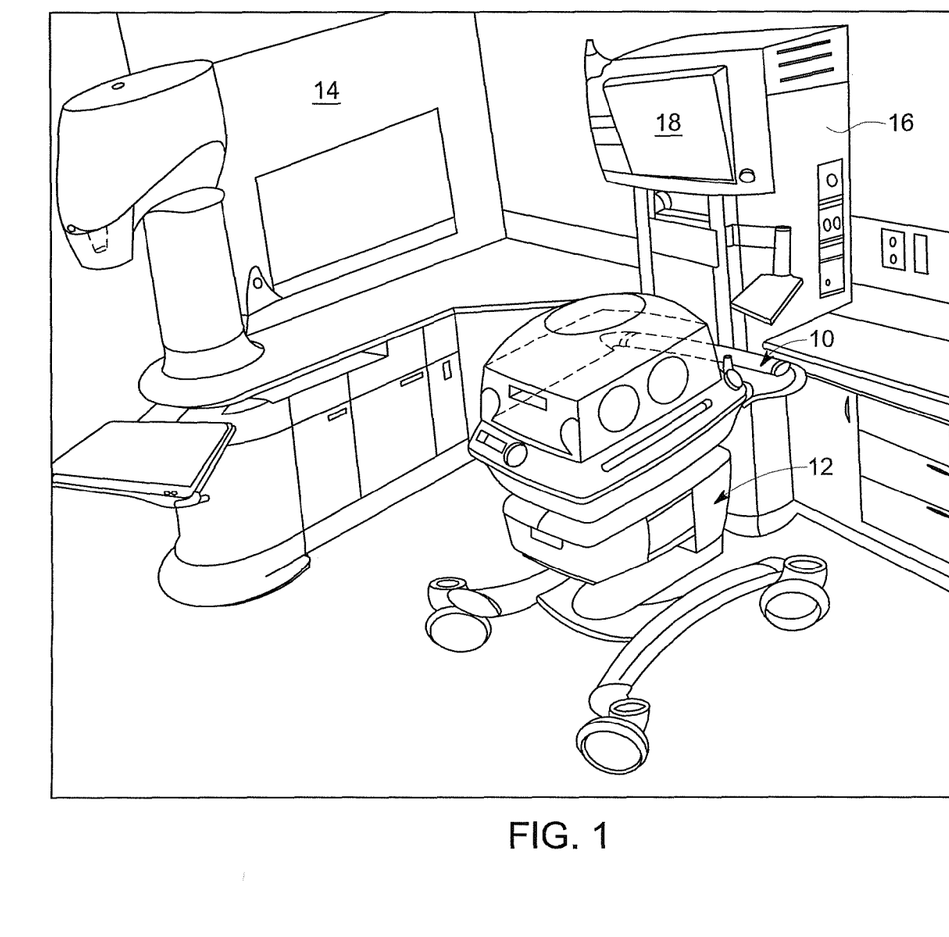
FIG. 1 is an environmental view that depicts an exemplary embodiment of an infant care station.

FIG. 1 depicts an environmental view of an infant care station 10. The infant care station 10 is depicted in this embodiment as an incubator; however, it will be recognized and understood from the disclosure and examples given herein that alternative embodiments of the infant care station 10 may include, but are not limited to, a hybrid warmer/incubator apparatus.

The infant care station 10 includes a mobile base 12 such that the infant care station 10 can be moved about a medical care facility, exemplarily into a neonatal intensive care unit (NICU) 14. In the embodiment depicted in FIG. 1, the infant care station 10 is communicatively connected to a NICU workstation 16 that in embodiments provide additional functionality and data connections to the infant care station 10. The NICU workstation 16 can include a graphical display 18 that presents patient information to a clinician. As detailed herein, the graphical display 18 may be a touch-sensitive graphical display.

Figure 2:
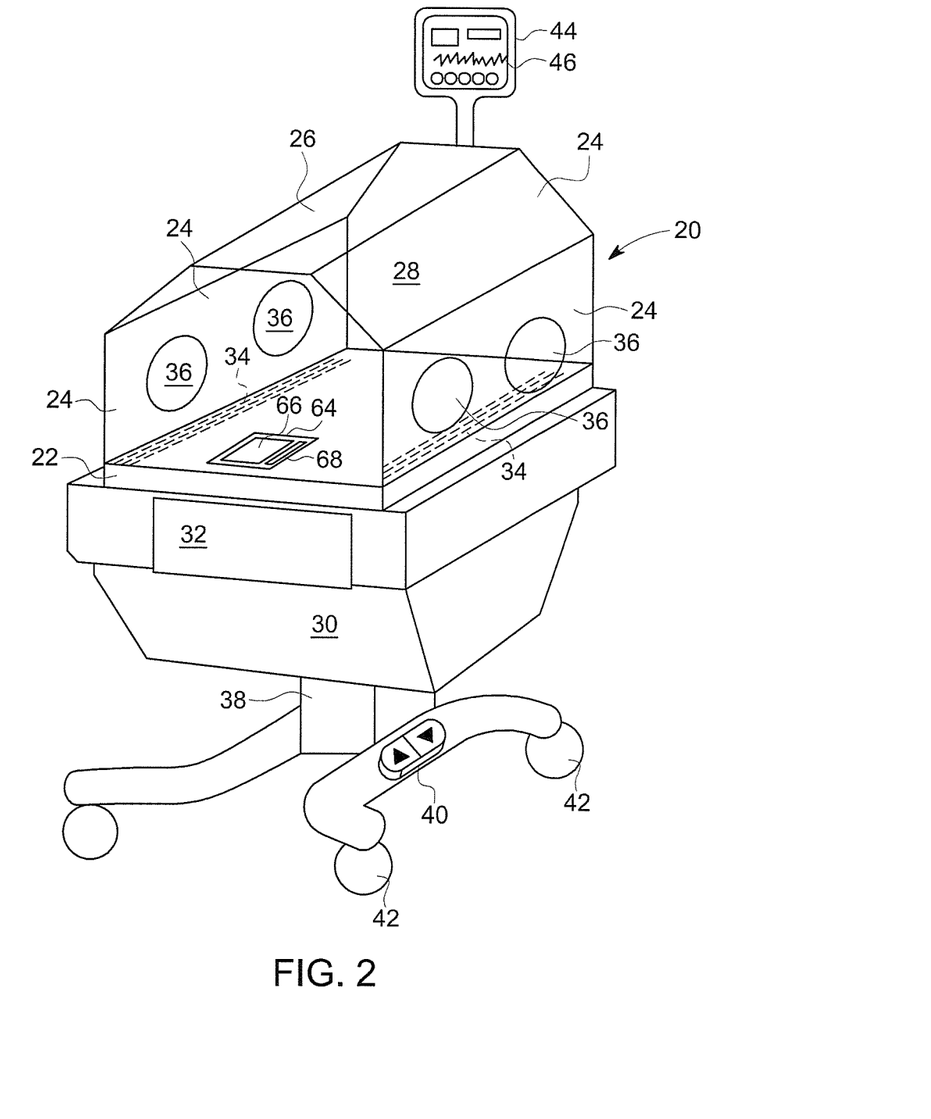
FIG. 2 depicts an exemplary embodiment of an infant care station.

FIG. 2 depicts an exemplary embodiment of an infant care station in which the infant care station is an incubator 20. The incubator 20 includes a horizontal surface 22 that is configured to support an infant patient (not depicted). It is to be understood that the incubator 20 may have the ability or control to move, rotate, or incline the horizontal surface 22; however, it will be understood that the horizontal surface 22 will generally remain horizontal such as to minimize movement of the infant patient within the incubator 20 due to gravity.

One or more walls 24 extend generally vertically from the horizontal surface 22. In the embodiment depicted in FIG. 1 of the incubator 20, four walls extend vertically from the horizontal surface 22 to define the rectangular shape of the incubator 20. However, it will be understood that in alternative embodiments, various numbers of walls 24 may be used to define the incubator into various geometric shapes which may include, but are not limited to, circles or hexagons. The incubator 20 further includes a canopy 26 that extends over the horizontal surface 22. In some embodiments, as depicted in FIG. 2, the canopy 26 may include multiple components or surfaces, or, as depicted in FIG. 1, the canopy may be curved or domed in shape.

While the incubator of FIG. 2 is depicted with the horizontal surface 22, walls 24, and canopy 26 being integrally connected, it will be understood that in alternative embodiments, including those described in greater detail herein, the horizontal surface 22, walls 24, and canopy 26 may be individual components that also may be moveable with respect to each other.

The horizontal surface 22, walls 24, and canopy 26 define a microenvironment 28 contained within these structures. The incubator 20 is configured such that the microenvironment 28 surrounds the infant patient (not depicted) such that the infant patient is only exposed to a controlled combination of environmental conditions selected by a clinician to promote the health and wellbeing of the infant patient.

The incubator 20 includes a base 30 that houses a convective heater 32. The convective heater 32 is operated as disclosed herein such that air is drawn into the incubator 20, at which point the air may be filtered or sterilized in another manner, including the use of UV light before being passed by heating coils (not depicted) to heat the air to a target or set point temperature. The sterilized and heated air is blown into the microenvironment 28 through vents 34 which, in an embodiment, are arranged along the walls 24. As is also known, the air may be entrained with supplemental gasses such as oxygen or may have added humidity such as to control these conditions within the microenvironment 28.

The walls 24 further include arm ports 36 that permit a clinician access into the microenvironment 28. While facilitating clinician access to the microenvironment 28, the arm ports 36, or the hands/arms of the clinician reaching into the microenvironment 28 through the arm ports 36, can be a source of introducing bacterial or viral contamination into the microenvironment. This can create an infection risk to the infant patient. Therefore in use, a hospital or medical care facility may have sanitary requirements such as, but not limited to, washing with antibacterial soap, use of gloves or other forms of hand sanitizing by the clinician before accessing the microenvironment 28 through the arm ports 36. As previously described, some embodiments of the incubator 20 may align the vents 34 along the walls 24 in such a manner as to produce vertical jets of air along the walls 24. These vertical jets of air further create a barrier across the arm ports 36 against transmission of viral or bacterial contaminants through the arm ports 36 from outside the microenvironment 28. It has been observed that these requirements can present a problem to a clinician who accesses the microenvironment only to determine that an adjustment or control of an incubator feature or function is needed, requiring use of non-sterile control equipment.

Embodiments of the incubator 20 further include a pedestal 38 connected to the base 30. The pedestal 38 includes mechanical components (not depicted), which may include, but are not limited to, servo motors, rack and pinion systems, or screw gear mechanisms that are operable by foot pedals 40 to raise or lower the base 30, effectively raising or lowering the position of the infant patient (not depicted) in relation to the clinician. As previously disclosed, the incubator 20 may be moveable by wheels or casters 42 connected to the pedestal 38.

Figure 5:
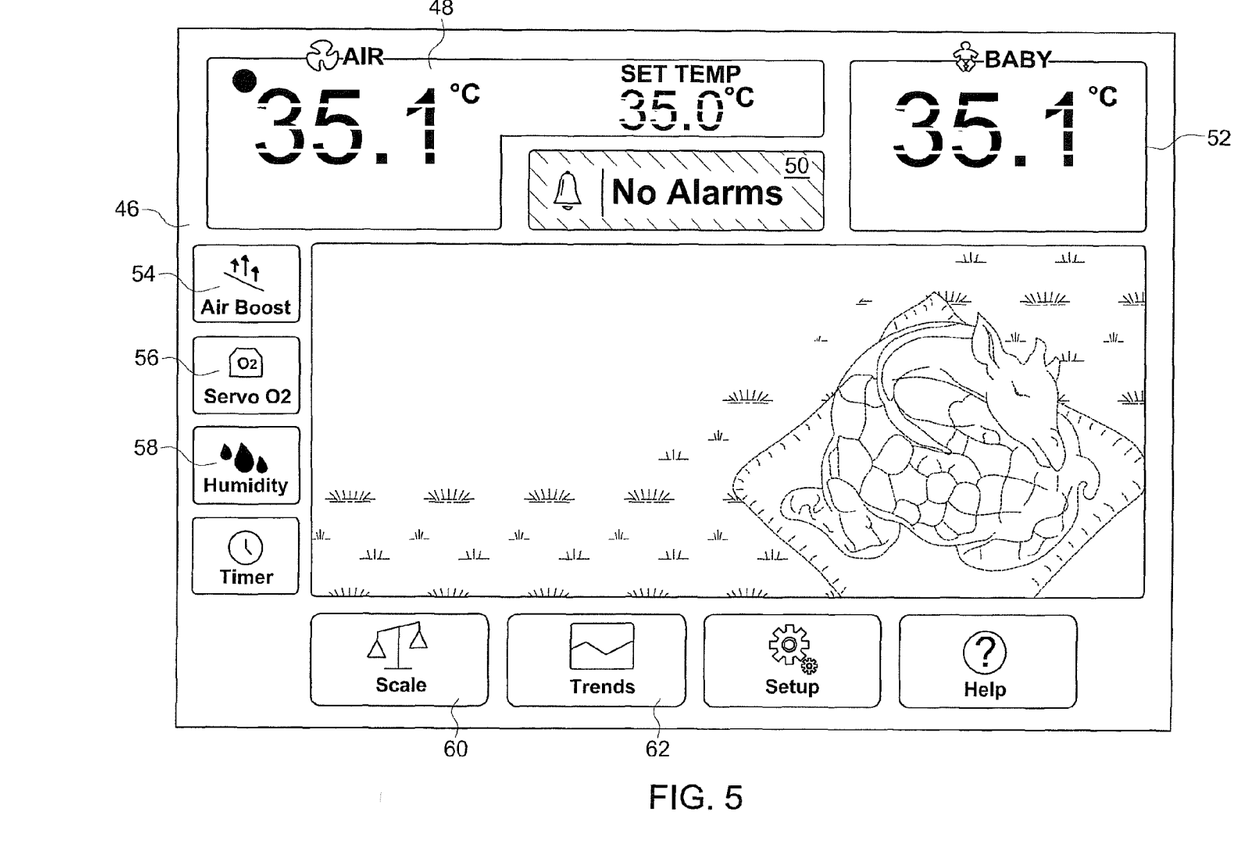
FIG. 5 depicts an exemplary embodiment of a graphical user interface.

The exemplary embodiment of the incubator 20 depicted in FIG. 2 includes a graphical display 44 that is mounted to a wall 24 or the canopy 26 of the incubator 20 at a position external to the microenvironment 28. The graphical display 44 is operated by a processor (not depicted) to present a graphical user interface (GUI) 46. A non-limiting example of which is depicted in FIG. 5. In an embodiment, the graphical display 44 is a touch-sensitive graphical display and the GUI 46 is configured to specifically respond to inputs made by a clinician received through the touch-sensitive graphical display. During normal operation, the touch-sensitive graphical display 44 and touch-sensitive configured GUI 46 are used to control various functions of the incubator 20. With reference to FIG. 5, the GUI 46 presents a variety of information, such as the air temperature 48 and an alarm indication 50.

Non-limiting examples of the alarms that may be presented at 50 can include, but are not limited to, threshold indications for physiological parameters such as tachycardia, bradicardia, excessive or insufficient respiration rate, excessive or insufficient temperature or disconnection of a physiological monitoring sensor. The GUI 46 further presents the temperature of the infant patient 52. The GUI 46 further presents a variety of controls such as, but not limited to, control of the air boost 54, which in an embodiment refers to the aforementioned jets of air provided along the walls 24 by the vents 34. The supplemental oxygen 56 operation of a scale function 60 and a presentation of measured patient trends 62. In embodiments, the patient trends 62 may present various physiological measurements obtained from the infant patient over time. The physiological measurements may include, but are not limited to, temperature, respiration rate, nutrition, weight or other information as may be recognized by one skilled in the art.

Referring back to FIG. 2, an auxiliary input device 64 is located within the microenvironment 28. The auxiliary input device 64 solves the aforementioned problem of a clinician performing a sanitation procedure before accessing the microenvironment only to identify that a parameter change is required that requires operation of the touch-sensitive graphical display 44 in order to input such change to the touch-sensitive configured GUI 46. The auxiliary input device 64 can be activated by the clinician and, as described herein, the processor (not depicted) can change the function and operation of the GUI such that the clinician can interact with the GUI 46 through inputs and controls entered with the auxiliary input device 64.

In the embodiment depicted in FIG. 2, the auxiliary input device 64 includes a touch-sensitive track pad 66 and a button 68. It will be understood that this is a non-limiting example, and other embodiments of the auxiliary input device may include only a track pad, only a button, or multiple track pads and/or buttons. In embodiments, the track pad 66 may be a touch-sensitive panel that may or may not include an integrated graphical display and its own graphical user interface (not depicted). In still further embodiments, the auxiliary input device 64 may rather be an image capture device, such as a video camera (not depicted) that is operable to perform image captures of various clinician hand gestures that may serve as inputs to the processor in conjunction with the GUI 46.

Figure 6:
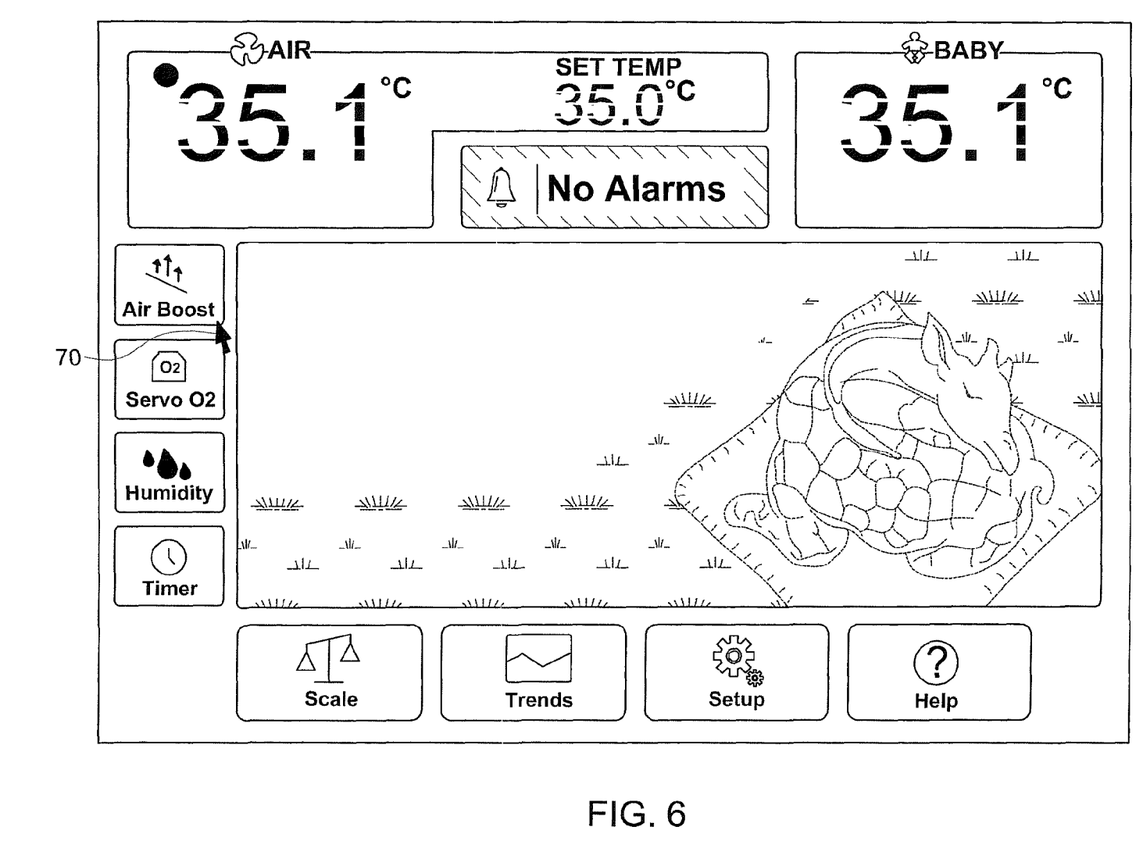
FIG. 6 depicts an alternative exemplary embodiment of a graphical user interface.

As will be explained in further detail herein, the activation of the auxiliary input device 64 by the clinician may cause the processor (not depicted) to modify the GUI 46 presented on the graphical display 44, such that the GUI 46 is no longer configured for a touch-sensitive input, but rather presents a cursor 70 such as depicted in FIG. 6 that moves responsive to input commands provided at the auxiliary input device 64.

Figure 3:
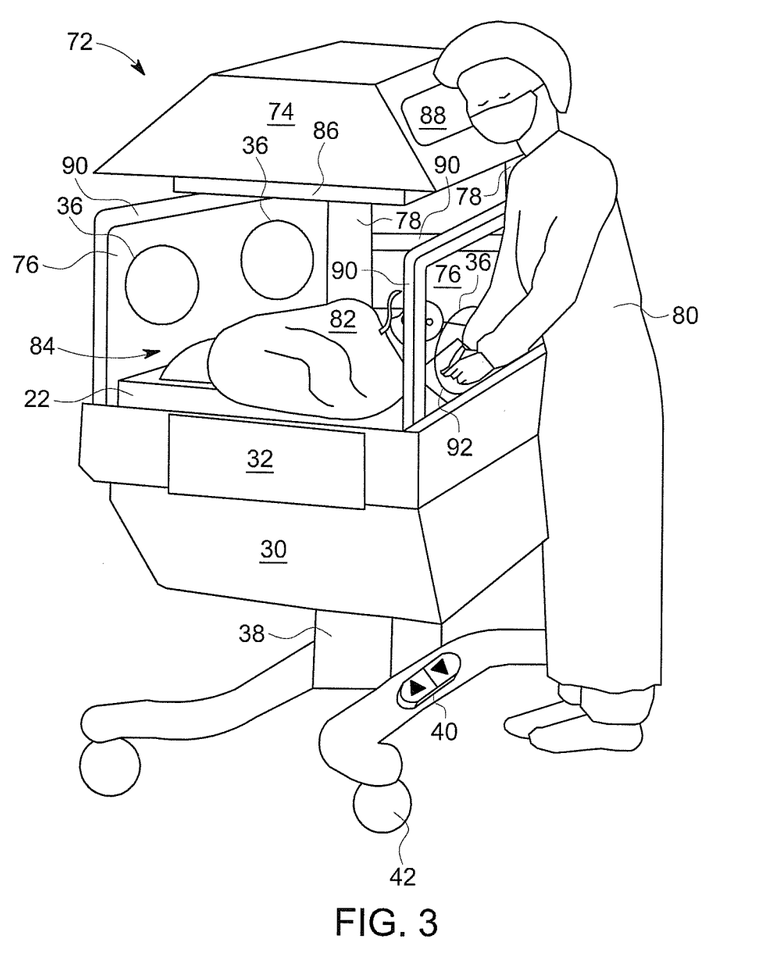
FIG. 3 depicts an alternative exemplary embodiment of an infant care station.

FIG. 3 depicts an alternative embodiment of an infant care station in which the infant care station is a hybrid infant care station 72 that can functionally operate as either a warmer or an incubator. In a hybrid infant care station 72, the canopy 74 is separate from the walls 76. The canopy 74 is vertically moveable with respect to the walls 76 and the horizontal surface 22 on vertical rails 78. The walls 76 include one or more arm ports 36 through which the clinician 80 can access the infant patient 82 located in the microenvironment 84 defined by the horizontal surface 22, walls 76, and canopy 74. It will be recognized that like reference numerals will be used between like structures found in FIGS. 2 and 3 in order to promote efficiency in the description.

The hybrid infant care station 72 is operable between incubator and warmer modes. When the hybrid infant care station 72 operates as a radiant warmer, the canopy 74 may be vertically separated along the rail 78 along the horizontal surface 22, and a radiant heater 86 located in the canopy 74 produces radiant heat energy that is directed downward at the infant patient 82, and thereby operates to control the temperature of the infant patient 82. When the hybrid infant care station 72 operates as an incubator, the canopy 74 is moved vertically closer to the horizontal surface 22 and the infant patient 82 thereby enclosing or partially enclosing the infant patient 82 in conjunction with the walls 76. In operation as an incubator, the hybrid infant care station 72 may control the temperature of the infant patient 82 with a convective heater 32, while in other embodiments, the convective heater 32 and the radiant heater 86 may work in conjunction in order to effectively control the temperature of the infant patient 82.

The embodiment of the hybrid infant care station 72 depicted in FIG. 3 includes a touch-sensitive graphical display 88 built into the canopy 74. The touch-sensitive graphical display 88 may operate in the manner as described above with respect to FIG. 2. It is also recognized that rather than being particularly located in the canopy 74, the touch-sensitive graphical display may alternatively be secured to the canopy rails 78 or a wall rail 90. However, in these instances, the touch-sensitive graphical display 88 is located outside of the microenvironment 84. Once the clinician 80 has gone through a sterilization procedure and is interacting with the infant patient 82 in the microenvironment 84, the clinician 80 can use the auxiliary input device 92 as described above, and as will be described in further detail herein, to input information and interact with a GUI presented on the touch-sensitive graphical display 88. As is shown in FIG. 3, the auxiliary input device 92 may be moveable within the microenvironment 84 such that the clinician 80 can move the auxiliary input device 92 to a convenient location or orientation for input use while still being able to attend to the infant patient 82.

Figure 4:
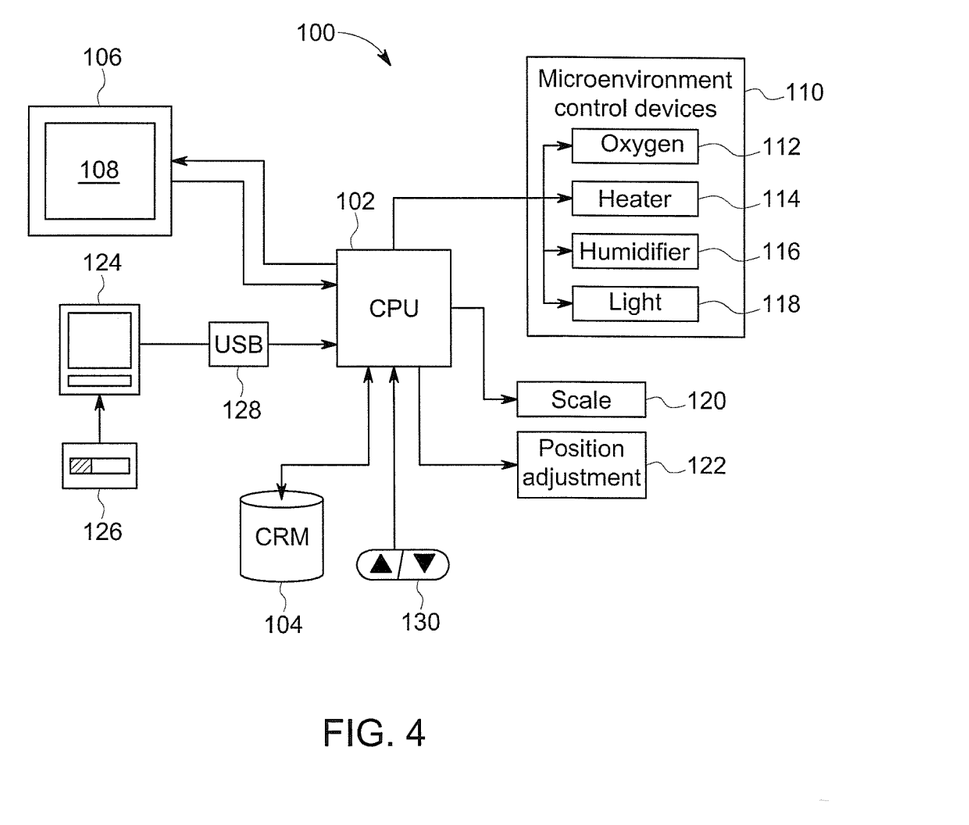
FIG. 4 depicts an exemplary system diagram of aspects of an infant care station.

FIG. 4 is a system diagram of an exemplary embodiment of electronic and/or functional components of an infant care station 100. A processor or CPU 102 is communicatively connected to the functional components and operates to carry out many of the functions as described herein. The processor 102 is communicatively connected to a computer readable medium 104 that includes volatile or nonvolatile memory upon which computer readable code is stored. The processor 102 accesses the computer readable code and the computer readable medium 104 upon executing the code carries out the functions as described herein. It is to be understood that while the computer readable medium 104 is depicted separate from the processor 102, the computer readable medium 104 may be a part of the processor 102 or integrally connected to the processor 102 while in still further embodiments the computer readable medium 104 may be implemented as a plurality of computer readable media for access by the processor 102.

The processor 102 is communicatively connected to a graphical display 106 which is configured to present a graphical user interface (GUI) 108. As disclosed herein, the graphical display 106 may be a touch-sensitive graphical display and thereby also operate as the user input device for the infant care station 100. In such an embodiment, the computer readable code stored on the computer readable medium 104 when executed by the processor 102 presents a GUI 108 that is configured to operate in accordance with a touch-sensitive inputs received by the graphical display 106.

As previously disclosed, the infant care station 100 may have a plurality of microenvironment control devices 110. Such microenvironment control devices may include the provision supplemental oxygen 112 such as by control of a source of medical oxygen gas, a heater 114 which may be a radiant heater, a convective heater, or both, a humidifier 116, or a light 118. As previously disclosed, the clinician interacts with the GUI, exemplarily through the touch-sensitive graphical display 106 in order to give commands to the microenvironment control devices 110 in order to control the environmental conditions within the microenvironment.

The infant care station 100 may further include other functional features including, but not limited to, a scale 120. Such a scale may be integrated into the horizontal surface of the infant care station to facilitate measurement and tracking of changes in the infant patient's weight. Embodiments of the scale 120 require that the clinician zero or tare the scale before weighing the infant patient. Such operations may require the clinician to lift the infant patient off of the horizontal surface, then initiate the zero or tare procedure of the scale 120 with an input to the graphical display 106, before returning the infant patient onto the horizontal surface to be weighed by the scale 120.

The infant care station 100 may further include position adjustment controls 122 that exemplarily operate servo motors that raise, lower, rotate or tilt at least a portion of the infant care station, and in particular, the horizontal surface of the infant care station. The infant care station 100 may include foot pedals 130 that a clinician operates by stepping upon or pressing with one's foot in order to provide an input to the processor 102 to send instructions to the position adjustment controls 122.

As previously disclosed, when efforts are made to maintain the microenvironment in a sterile or partially sterile condition in order to reduce or eliminate viral or bacterial exposure to the infant patient, the clinician must carry out a disinfection procedure to the clinician's hands and/or arms before placing them in the microenvironment. If the clinician must remove a hand and/or arm from the microenvironment, such as to input a control or command through the touch-sensitive graphical display 106, the clinician must either repeat the disinfection procedure or risk introducing infectious contaminants into the microenvironment. Of particular concern are user interfaces such as touch-sensitive displays that are known as sources for infection to breed and multiply. Therefore, the auxiliary input device 124, which is located within the microenvironment, is thus held in the same sterile conditions as the rest of the microenvironment and the clinician can interact and provide inputs and controls to the processor 102 through the auxiliary input device 124. As previously disclosed, embodiments of the auxiliary input device 124 may include a track pad or other touch-sensitive input device, a button, a video-capture device, or a combination thereof. Thus, the clinician can use various commands or gestures with such auxiliary input devices 124 in order to provide inputs and commands to the processor 102.

In an embodiment, a lock 126, which may be a physical component or locking device, is associated with the auxiliary input device 124. The lock 126 must be manipulated by the clinician in order to activate the input device 124. In non-limiting examples, the lock 126 may be a mechanical or electro-mechanical switch, slide, or button that turns on the auxiliary input device 124. In alternative embodiments, the lock 126 may restrict access to the auxiliary input device such as with a cover or shielding device.

In alternative embodiments, the lock 126 is implemented by the processor 102 executing computer software. In such an embodiment, the auxiliary input device 124 may be held in an inactive or dormant state prior to receiving an input on the exemplary touchpad or button when such an input signal is received by the processor 102, then the processor 102 executes computer readable code to activate or "wake up" the auxiliary input device and receive clinician input therefrom. Still further embodiments may include an unlocking gesture or code that is entered through the auxiliary input device 124 before the auxiliary input device is activated such that the processor 102 receives and acts upon clinician inputs to the auxiliary input device 124.

In exemplary embodiments, upon activation or unlocking of the auxiliary input device 124, the processor 102 executes computer readable code such as to change the operation of the processor 102, touch-sensitive graphical display 106 and/or GUI 108. In one embodiment, the processor 102 may disable the touch-sensitive features of the display 106 and similarly adjust the GUI 108 to operate in a manner suitable for use with the auxiliary input device 124. One such example is shown between FIGS. 5 and 6, wherein FIG. 5 represents an exemplary touchscreen GUI, while FIG. 6 represents an exemplary GUI when a touchscreen is inactive. As the GUI in FIG. 6 does not receive touch-sensitive inputs, a cursor 70 or other such icon is required that can be manipulated through inputs through the auxiliary input device 124 in order to interact with the GUI of FIG. 6. Furthermore, in order to avoid confusion, the processor 102 can operate the display 106 or the GUI 108 in a manner such as to activate or inactivate the touch-sensitive inputs such that only a single device or platform for clinician inputs are available at a single time. In embodiments, this can reduce confusion between clinicians of which clinician has control of the infant care station 100. In alternative embodiments, the processor and the GUI 108 operate in response to the activation or unhooking of the auxiliary input device to add the auxiliary input device functionality while maintaining the touch-sensitive aspects operational.

In some embodiments, the GUI 108 may be modified by the processor 102 when the auxiliary input device 124 is activated such that the GUI presents a reduced set of functionality as more conducive to only those functionalities that a clinician would want to control or adjust while the clinician's hands are in the microenvironment. Such functionalities may include, but are not limited to, temperature set point, air vent control (air boost), oxygen concentration, humidity control, alarm silencing, and scale or infant patient weighing functions.

In the example of the scale or weighing functions, the auxiliary input device 124 can facilitate the weighing of the infant patient as the clinician can lift the infant patient off of the horizontal surface that includes the scale or weighing device 120. With the infant patient removed from the scale 120 the clinician can activate the scale zero or tare feature using the auxiliary input device 124 before returning the infant patient to the horizontal surface for weighing by the scale 120. Thus, in this example, the clinician need not be concerned with introducing exterior contaminations to microenvironment when performing a zero or tare feature of the scale 120 and the clinician can have both hands in the microenvironment attending to the infant patient.

In a still further embodiment, the activation of the auxiliary input device 124 can cause the processor 102 to add functionality to the GUI 108. One specific example of this is that when the clinician's hands are in the microenvironment, it may be ergonomically uncomfortable for the clinician to activate the foot pedals 130 in order to adjust the height of the infant patient relative to the clinician. Furthermore, the clinician may not identify that the patient is too low or too high such that the clinician is uncomfortable working on the infant patient until the clinician has gone through a sterilization procedure and the clinician's hands are in the microenvironment. Therefore, the processor 102 can operate the GUI 108 in order to present position adjustment controls on the GUI 108 that are operable through clinician inputs to the auxiliary input device 124. In such an embodiment, the processor 102 may disable the foot pedals 130 while the auxiliary input device 124 is operational, such that the foot pedals 130 are not inadvertently activated.

Some embodiments of the infant care system 100 may connect the auxiliary input device 124 to the processor 102 through a USB port or other similar data connection 128. In such embodiments, the processor side of the data connection 128 may be located in the horizontal surface or another component of the infant care system that faces the microenvironment. An embodiment of the auxiliary input device 124 has a mating plug that connects with the data connection 128. This arrangement may facilitate removal of the auxiliary input device 124 for maintenance, cleaning, or sterilization procedures. Additionally, if the auxiliary input device side of the data connection is attached to a cord, this can facilitate movement of the auxiliary input device 124 within the microenvironment such that the clinician can move the auxiliary input device 124 to a convenient location for both clinician use as an input device and to facilitate clinician access to the infant patient.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An infant care station comprising:
   a horizontal surface configured to support an infant patient;
   at least one wall extending generally vertically from the horizontal surface, the horizontal surface and at least one wall defining a microenvironment about the infant patient;
   a touch-sensitive display mounted to the infant care station at a location external to the microenvironment;
   a processor that operates the touch-sensitive display to present a graphical user interface (GUI);
   an auxiliary input device located within the microenvironment and communicatively connected to the processor, the auxiliary input device configured to receive a clinician input, and the processor is configured to operate the touch-sensitive display based upon the clinician input; and
   a lock on the auxiliary input device operable between a first condition wherein the auxiliary input device is disabled and a second condition wherein the auxiliary input device is operational to receive an input to the GUI,
   wherein when the lock is in the first condition, the processor operates the touch-sensitive display and the GUI to receive the clinician input as a touch input and when the lock is in the second condition, the processor operates the touch-sensitive display to present the GUI with a cursor and the auxiliary input device is configured to receive a clinician input to move the cursor on the GUI.

2. The infant care station of claim 1, further comprising a canopy positioned above the horizontal surface, the canopy defining an upper limit to the microenvironment.

3. The infant care station of claim 2, further comprising:
   arm ports through the at least one wall to permit access by a clinician into the microenvironment; and
   air vents arranged on the horizontal surface along the at least one wall to create an air barrier across the arm ports;
   wherein the microenvironment is maintained as an environment sterile to contaminants external to the microenvironment.

4. The infant care station of claim 1, wherein the lock is a mechanical lock.

5. The infant care station of claim 1, wherein when the lock is in the first condition, the auxiliary input device is operable to receive an unlocking input, wherein upon receiving the unlocking input the auxiliary input device lock operates in the second condition.

6. The infant care station of claim 1 wherein the graphical user interface presents controls for environmental set points of the microenvironment, alarm silencing, and weighing functions.

7. The infant care station of claim 1 wherein the auxiliary input device is movable within the microenvironment.

8. The infant care station of claim 7, wherein the auxiliary input device is communicatively connected to the processor in a removable manner.

9. The infant care station of claim 8, further comprising a USB port communicatively connected to the processor and accessible from the microenvironment and the auxiliary input device is removably connected to the USB port.

10. An infant care station comprising:
a horizontal surface configured to support an infant patient;
at least one wall extending generally vertically from the horizontal surface, the horizontal surface and at least one wall defining a microenvironment about the infant patient;
a touch-sensitive display mounted to the infant care station at a location external to the microenvironment;
a processor that operates the touch-sensitive display to present a graphical user interface (GUI);
an auxiliary input device located within the microenvironment and communicatively connected to the processor, the auxiliary input device configured to receive a clinician input, and the processor is configured to operate the touch-sensitive display based upon the clinician input; and
a lock on the auxiliary input device operable between a first condition wherein the auxiliary input device is disabled and a second condition wherein the auxiliary input device is operational to receive an input to the GUI, and wherein when the lock is in the first condition, the GUI presents a full functionality and when the lock is in the second condition, the GUI presents a reduced functionality.

11. The infant care station of claim 10, further comprising position controls positioned external to the microenvironment, and when the lock is in the first condition, the position controls are operable to control a position of the horizontal surface of the infant care station and when the lock is in the second condition, the position controls are disabled and the position of the horizontal surface is controlled with the auxiliary input device through the GUI.

12. An infant care station for maintaining environmental conditions about an infant patient, the infant care station comprising:
a horizontal surface configured to support an infant patient;
at least one wall extending generally vertically from the horizontal surface;
a canopy positioned above the horizontal surface and extending generally parallel to the horizontal surface;
a microenvironment defined by the horizontal surface, the canopy, and the at least one wall;
a touch-sensitive display mounted to the infant care station at a location external to the microenvironment;
a processor communicatively connected to the touch-sensitive display and configured to operate the touch-sensitive display to present a touch-sensitive graphical user interface (GUI);
an auxiliary input device positioned within the microenvironment and communicatively connected to the processor, such that upon activation of the auxiliary input device, the processor presents a cursor in the touch-sensitive GUI and inputs to the auxiliary input device to control the cursor within the touch-sensitive GUI; and
position controls positioned external to the microenvironment and operable to control a position of the horizontal surface of the infant care station;
wherein upon activation of the auxiliary input device, the processor disables the position controls and the position of the horizontal surface is controlled with the auxiliary input device through the touch-sensitive GUI.

13. The infant care station of claim 12, further comprising:
arm ports through the at least one wall to permit access by a clinician into the microenvironment; and
air vents arranged on the horizontal surface along the at least one wall to create an air barrier across the arm ports;
wherein the microenvironment is maintained as an environment sterile to contaminants external to the microenvironment.

14. The infant care station of claim 12, further comprising:
a heater operated by the processor to maintain a temperature of the microenvironment;
wherein the processor receives input commands to control a temperature set point for the heater through the touch-sensitive GUI.

15. The infant care station of claim 12, further comprising:
a scale operated by the processor to measure a weight on the horizontal surface;
wherein the processor receives input commands to control an operation of the scale through the touch-sensitive GUI.

16. The infant care station of claim 12 wherein the auxiliary input device is removably connected to the infant care station at a position within the microenvironment.

17. The infant care station of claim 12, wherein the auxiliary input device is an input device selected from a track ball, a track pad, or a video capture device.

18. An infant care station for maintaining environmental conditions about an infant patient, the infant care station comprising:
a horizontal surface configured to support an infant patient;
at least one wall extending generally vertically from the horizontal surface;
a canopy positioned above the horizontal surface and extending generally parallel to the horizontal surface;
a microenvironment defined by the horizontal surface, the canopy, and the at least one wall;
a touch-sensitive display mounted to the infant care station at a location external to the microenvironment;
a processor communicatively connected to the touch-sensitive display and configured to operate the touch-sensitive display to present a touch-sensitive graphical user interface (GUI);
an auxiliary input device positioned within the microenvironment and communicatively connected to the processor, such that upon activation of the auxiliary input device, the processor presents a cursor in the touch-sensitive GUI and inputs to the auxiliary input device control the cursor within the touch-sensitive GUI,
wherein upon activation of the auxiliary input device, the processor controls the touch-sensitive GUI to present a reduced set of functionalities for input from the auxiliary input device.

* * * * *